United States Patent
Kubota

Patent Number: 5,071,888
Date of Patent: Dec. 10, 1991

[54] CARBAZOLE PHOTOINITIATORS FOR THE PHOTOPOLYMERIZATION OF UNSATURATED COMPOUNDS

[75] Inventor: Naohiro Kubota, Ageo, Japan

[73] Assignee: Asahi Denka Kogyo K.K., Saitama, Japan

[21] Appl. No.: 753,000

[22] Filed: Jul. 8, 1985

[30] Foreign Application Priority Data

Jul. 10, 1984 [JP] Japan .................................. 59-142792

[51] Int. Cl.$^5$ .......................... C08F 2/46; C08G 0/00; C08J 3/28; C07D 401/00
[52] U.S. Cl. ....................................... 522/34; 522/36; 522/39; 522/10; 522/8; 544/142; 544/80; 544/106; 544/357; 546/187
[58] Field of Search ................. 544/142, 80, 106, 357; 546/187; 514/934; 522/39, 36, 10, 8, 34

[56] References Cited

U.S. PATENT DOCUMENTS

| | | | |
|---|---|---|---|
| 4,167,464 | 9/1979 | George | 522/34 |
| 4,559,371 | 12/1985 | Hüsler et al. | 522/39 |
| 4,861,916 | 8/1989 | Köhler et al. | 522/39 |

*Primary Examiner*—C. Warren Ivy
*Assistant Examiner*—Raymond Covington

[57] ABSTRACT

Photopolymerizable prepolymer compositions are provided comprising an unsaturated compound having at least one ethylenic double bond that is photopolymerizable to form a polymer, and a photoinitiator having one of the formulae:

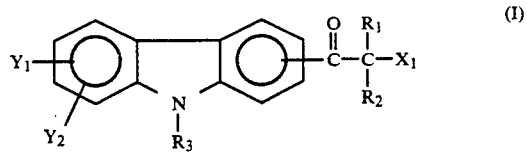

(I)

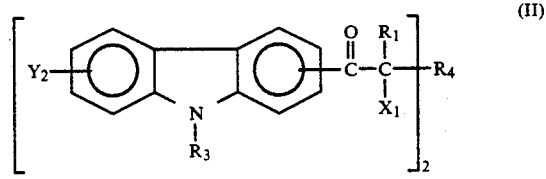

(II)

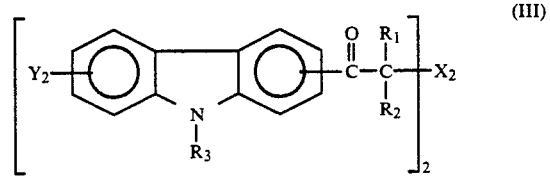

(III)

11 Claims, No Drawings

CARBAZOLE PHOTOINITIATORS FOR THE PHOTOPOLYMERIZATION OF UNSATURATED COMPOUNDS

Photochemical polymerization processes have attained substantial importance in the art, especially in those cases where thin layers have to be hardened in a short time, for example, in the hardening of varnish coatings, or in the drying of printing inks.

Many compounds are known as photoinitiators for the photopolymerization of unsaturated compounds. Aromatic ketones such as benzophenone are most commonly used, due to their excellent solubility to unsaturated compounds. Recently, α-substituted aromatic aliphatic ketones were proposed as photoinitiators in U.S. Pat. No. 4,308,400, and sulfur-containing-α-amino-aromatic-aliphatic ketones were proposed as photoinitiators in Japan Kokai No. 83-157805.

Many of these known photoinitiators have the shortcoming that when mixed with an unsaturated compound they display an insufficient storage life. Furthermore, these photoinitiators tend to cause an undesirable yellowing of the polymerized composition, and they are insufficiently reactive, as evidenced by a relatively long polymerization time. Some are rapidly inactivated by atmospheric oxygen. There is therefore a need in the art for photoinitiators which are readily soluble in the substrate, and which, having a good storage life in the dark, initiate the photopolymerization more rapidly and give a higher polymer yield per unit of time, than the known photoinitiators.

In accordance with this invention, carbazole photoinitiators are provided having the following formulae (I), (II) and (III) that possess the required properties as photoinitiators. In particular, they effect a rapid photopolymerization, and either do not display the shortcomings referred to, or display them to a much lesser degree, than the known photoinitiators. Furthermore, they are suitable for the photochemical crosslinking of polyolefins.

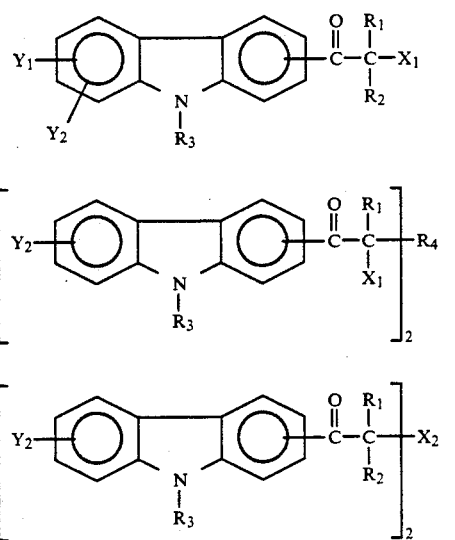

wherein:
$R_1$ and $R_2$ are each alkyl having from one to about eighteen carbon atoms; or are taken together to form alkylene having from about two to about twelve carbon atoms;

$R_3$ is selected from the group consisting of hydrogen; alkyl having from one to about eighteen carbon atoms; and acyl having from about two to about twelve carbon atoms;

$X_1$ is —$OR_5$ or

in which $R_5$ is selected from the group consisting of hydrogen; alkyl and alkenyl having from one to about eighteen carbon atoms; and $R_6$ and $R_7$ are selected from the group consisting of alkyl; hydroxyalkyl having from one to about eighteen carbon atoms; and $R_6$ and $R_7$ taken together to form alkylene having from about two to about twelve carbon atoms; and oxadialkylene and iminodialkylene having from four to about twenty-four carbon atoms;

$Y_1$ is hydrogen or

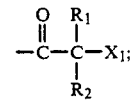

$Y_2$ is selected from the group consisting of hydrogen, halogen, and nitro;

$R_4$ is a direct linkage (—) or alkylene having from about two to about twelve carbon atoms;

$X_2$ is —O—$R_8$—O— or

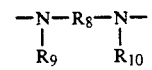

in which:
$R_8$ is alkylene having from about two to about twelve carbon atoms;
$R_9$ and $R_{10}$ are alkyl having from one to about eighteen carbon atoms; or are taken together to form alkylene having from about two to about twelve carbon atoms.

Exemplary $R_1$, $R_2$, $R_3$, $R_5$, $R_6$, $R_7$, $R_9$ and $R_{10}$ alkyl are methyl, ethyl, propyl, isopropyl, butyl, sec-butyl, t-butyl, isobutyl, amyl, sec-amyl, isoamyl, tert-amyl, hexyl, isohexyl, sec-hexyl, tert-hexyl, heptyl, isoheptyl, tert heptyl, sec-heptyl, octyl, isooctyl, 2-ethylhexyl, nonyl, isononyl, tert-nonyl, decyl, undecyl, dodecyl, tridecyl, tetradecyl, heptadecyl and octadecyl.

Exemplary $R_1$ and $R_2$ taken together as alkylene include ethylene, propylene, butylene, amylene, hexylene heptylene, octylene, nonylene, decylene and dodecylene.

Exemplary $R_3$ acyl include acetyl, propionyl, butyroyl, valeroyl, caproyl, 2-ethylhexanoyl, decanoyl and lauroyl; acryloyl, methacryloyl, vinylacetyl, benzoyl, toluoyl, t-butylbenzoyl and chlorobenzoyl.

Exemplary $R_5$ alkenyl include allyl and octadecenyl.

Exemplary $R_6$ and $R_7$ hydroxyalkyl include hydroxyethyl, 2-hydroxypropyl and 2-hydroxybutyl, 2-hydroxyhexyl, 2-hydroxyoctyl, 2-hydroxynonyl, and 2-hydroxydodecyl.

Exemplary $R_6$ and $R_7$ alkylene, oxadialkylene and iminodialkylene include ethylene, propylene, butylene, amylene, hexylene, heptylene, octylene, decylene and dodecylene, oxadiethylene and iminodiethylene.

Exemplary $Y_2$ halogen include chlorine, bromine, fluorine and iodine.

Exemplary $R_4$ alkylene include methylene, ethylene, trimethylene, tetramethylene, hexamethylene, octamethylene, decamethylene and dodecamethylene.

Exemplary $R_8$ alkylene include ethylene, propylene, 2,2-dimethylpropylene, 1,4-butylene, hexamethylene and decamethylene.

Exemplary $R_9$ and $R_{10}$ alkylene include methylene, ethylene, propylene, butylene, amylene, hexylene, octylene, decylene and dodecylene.

The following are carbazole compounds of the formulae (I), (II) and (III) falling within the invention.

1. 3-(2-methyl-2-dimethylaminopropionyl) carbazole
2. 3-(2-methyl-2-morpholinopropionyl)-9-methylcarbazole
3. 3,6-bis(2-methyl-2-morpholinopropionyl)-9-methylcarbazole
4. 3-(2-methyl-2-morpholinopropionyl)-9-butylcarbazole
5. 3-(2-ethyl-2-piperidinopropionyl)-9-butylcarbazole
6. 3-(2-methyl-2-diethanolaminopropionyl)-9-methylcarbazole
7. 3-(2-methyl-2-dibutylaminopropionyl)-6-chlorocarbazole
8. 3-(2-methyl-2-piperidinopropionyl)-6-nitro-9-methylcarbazole
9. 3-(2-methyl-2-morpholinopropionyl)-9-acetylcarbazole
10. 3,6-bis(2-methyl-2-morpholinopropionyl)-9-benzoylcarbazole
11. 3-(2-methyl-2-hydroxypropionyl)-9-methylcarbazole
12. 3-(2-methyl-2-methoxypropionyl)-9-methylcarbazole
13. 3-(2-methyl-2-allyloxypropionyl)-9-methylcarbazole
14. 3-(1-hydroxycyclohexanoyl)-9-butylcarbazole
15. 1,4-bis(9-butyl-3-carbazolyl)-2,3-dihydroxybutane-1,4-dione
16. 1,6-bis(9-methyl-3-carbazolyl)-2,5-bis(diethylamino) hexane-1,6-dione
17. 1,4-bis(1-(9-methyl-3-carbazolyloyl) isopropyl) piperidine
18. N,N'-dimethyl-N,N'-bis(1-(9-methyl-3-carbazolyloyl) isopropyl) ethylenediamine
19. 2,7-bis(1-(9-butyl-3-carbazolyloyl) isopropyl)-2,7-dimethyl-3,6-dioxaoctanol The carbazole compounds of formulae (I), (II) and (III) can be readily prepared by known procedures, for example, by the method described in U.S. Pat. No. 4,308,400.

The compounds of formulae (I) and (III) can be prepared by brominating the compound shown below, reacting the resulting compound with H—$X_1$ or H—$X_2$—H:

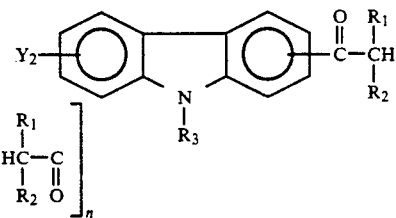

(n = 0 or 1)

The compounds of the formula (II) can be prepared by brominating the compound shown below, reacting the resulting compound with H—$X_1$.

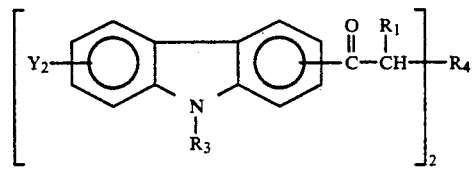

The following example is illustrative:

EXAMPLE I

Synthesis of 3-(2-methyl-2-morpholinopropionyl)-9-methylcarbazole

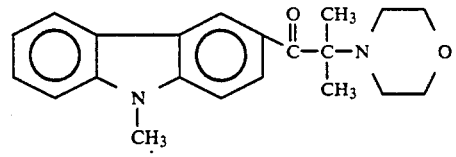

3-(2-Methylpropionyl)-9-methylcarbazole 15 g was dissolved in 50 ml of carbon tetrachloride. A solution of 12 g of bromine in 30 ml of carbon tetrachloride was added dropwise over one hour at room temperature, and the reaction mixture then stirred for one additional hour at room temperature. Then nitrogen gas was introduced to remove the hydrogen bromide produced and excess bromine.

Morpholine 30 g was added to the reaction mixture, which was then heated up to 120° C., while carbon tetrachloride was distilled off. The solution was stirred for 3 hours at 120° C., and the morpholine hydrobromide filtered out, and excess morpholine distilled off.

Toluene 100 ml was added, and the solution was washed with water, and then extracted with aqueous 3N HCL solution. The HCl solution was neutralized by adding 3N NaOH solution, and then extracted with toluene. The toluene solution was washed with water, and then toluene was distilled off. The residue was recrystallized from ethanol. The desired product, melting at 164°-166° C., was obtained.

If desired, the photoinitiators of this invention can be combined with secondary and tertiary alkyl and hydroxyalkyl amines, which act as accelerators.

Such amines include, for example, triethanolamine, triisopropanolamine, methyl-diethanolamine, octyl-diethanolamine, dodecyl-diethanolamine, octadecyl-diethanolamine, dibutyl-ethanolamine, dioctyl-ethanolamine, methyl-hydroxyhexyl-octanolamine, diethanolaniline, diethanolamine, methyl-ethanolamine, butylethanolamine, dodecyl-ethanolamine, tetrahydroxyethyl-hexamethylenediamine, triethylamine, tributylamine, dimethylaminopropylamine, dimethylaniline, diethylamine, dibutylamine, dioctylamine, tetramethyl-ethylenediamine and Michler's ketone. Among these amines, the alkanolamines are preferable, due to their excellent effect.

The photoinitiators of this invention can polymerize or harden any unsaturated compounds containing at least one ethylenic double bond in the molecule, as monomers or prepolymers.

Such unsaturated compounds include, for example, unsaturated carboxylic acids, such as acrylic acid, methacrylic acid, itaconic acid, crotonic acid and maleic acid; esters or amides of such unsaturated carboxylic acids with mono- or poly-hydric alcohols or amines; methacrylates of polyhydroxyesters obtained from polyol and polycarboxylic acid; unsaturated polyesters or polyamides obtained from unsaturated dicarboxylic acids and polyols or polyamines; urethane acrylates obtained from urethane compounds containing isocyanate groups prepared from diisocyanates with polyols and hydroxyalkyl methacrylates; epoxyacrylates obtained from polyglycidyl ethers of bisphenols or polyols and methacrylic acid; polyesters obtained from glycidyl methacrylate and dicarboxylic acid; dimethacryl modified polyesters or polyamides obtained from polyesters or polyamides containing carboxyl groups and glycidyl methacrylate.

The unsaturated esters can be derived from mono- or polyhydric alcohols having from one to six hydroxyl groups and from one to eighteen carbon atoms, in an open aliphatic chain or carboxylic or heterocyclic ring, including methanol, ethanol, butanol, allyl alcohol, octanol, ethylene glycol, diethylene glycol, triethylene glycol, propylene glycol, neopentyl glycol, 1,4-butanediol, 1,3-butanediol, 1,6-hexanediol, glycerine, trimethylolpropane, trimethylolethane, tris(2-hydroxyethyl) isocyanurate, pentaerythritol, diglycerine, ditrimethylolpropane and dipentaerythritol; mono- or poly-amines include ammonia, methyl amine, butylamine.

The unsaturated amides can be derived from mono or polyamino amines having from one to six amino groups and from one to eighteen carbon atoms in an open aliphatic chain or carboxylic or heterocyclic ring, including octylamine, diethylamine, dibutylamine, ethylenediamine, diethylenetriamine, piperazine, 1,6-hexamethylenediamine and melamine.

Preferred examples of esters and amides of unsaturated carboxylic acids include methyl-, ethyl-, butyl-, isooctyl- and 2-hydroxyethyl-acrylate, methyl- and ethyl-methacrylate, ethylene glycol diacrylate, triethylene glycol diacrylate, 1,4-butanediol diacrylate, trimethylolpropane triacrylate, pentaerythritol triacrylate, pentaerythritol tetraacrylate, tris-(2-hydroxyethyl) isocyanurate triacrylate, dipentaerythritol tetraacrylate; dipentaerythritol, hexaacrylate, glycerine diacrylate, triethylene glycol dimethacrylate, pentaerythritol trimethacrylate, ethylene glycol dicrotonate, diallyl fumarate, bis(acryloyloxyethylphenyl)-propane, acrylamide, methacrylamide, ethylene-bis-(acrylamide), hexamethylene-bis-(acrylamide) and methylene-bis-(acrylamide).

Examples of other photopolymerizable compounds are diallyl phthalate, diallyl malonate, divinyl phthalate, vinyl acetate, isobutyl vinyl ether, ethylene glycol divinyl ether, styrene, acrylonitrile, triallyl isocyanurate and triallyl phosphate.

The photoinitiators of this invention are effective in small amounts, and the amount is not critical, but is selected to give the desired rate of photopolymerization according to the unsaturated compound used. Good results are obtained in amounts within the range from about 0.1 to about 20 parts by weight, based on 100 parts of above unsaturated compound. More than this can be used.

The photopolymerizable systems comprising the photoinitiator and unsaturated compound can contain other conventional additives, such as heat polymerization inhibitors, colorants or pigments, plasticizers, surface-protecting agents, and lubricants.

Heat-polymerization inhibitors include hydroquinone, p-methoxyphenol, pyrogallol, catechol, 2,6-di-t-butyl-p-cresol, $\beta$-naphthol, and t-butylhydroquinone.

Colorants or pigments include carbon black, metal (silver, aluminum) powder, chrome yellow, titanium white, talc, alumina, Milori Blue, Chrome Vermillion, Hansa yellow, Benzidine Yellow, Vulcan Orange, Permanent Orange, Lake Red C, Brilliant Carmine B, Rhodamin Lake, Eosine, Victoria Blue Lake, Phthalocyanine Blue, Phthalocyanine Green, Quinacridone Red, Dioxazine Violet and Methyl Violet.

The polymerization is carried out in the usual way, by irradiation with light. Suitable light sources are, for example, carbon arc, mercury high pressure lamp, xenon lamp, metal halide lamp, tungsten lamp, argon laser and helium-cadmium laser.

The following examples represent preferred embodiments of photopolymerization systems utilizing photoinitiators of formulae (I), (II) and (III). All parts indicated are by weight.

EXAMPLES 1 TO 9

A resin mixture composed of 75 parts of NK ester U-108A (urethane acrylate (m.w. = 1500) available from Shinnakamura Kagaku), 25 parts of 1,6-hexanediol diacrylate and 0.5 part of photoinitiator as indicated in Table I was applied to paper using a film-drawing device to a thickness of 50 m$\mu$. The films were irradiated with a mercury high pressure lamp (Toshiba; Model H-400P) for 15 seconds (distance = 12 cm). The pencil hardness of the hardened films was measured, and the results are shown in Table I.

TABLE I

| Example No. | Photoinitiator | Pencil hardness |
|---|---|---|
| Control 1 | Benzophenone | 6B |
| Control 2 | 1-(2-methyl-2-morpholino-propionyl)-4-methylthiobenzene | 3H |
| Example 1 | 3-(2-methyl-2-dimethylamino-propionyl) carbazole | 8H |
| Example 2 | 3-(2-methyl-2-morpholino-propionyl)-9-methylcarbazole | 9H |
| Example 3 | 3-(2-methyl-2-morpholino-propionyl)-9-butylcarbazole | 9H |
| Example 4 | 3-(2-methyl-2-dibutylamino-propionyl)-6-chlorocarbazole | 7H |
| Example 5 | 3-(2-methyl-2-morpholino-propionyl)-9-acetylcarbazole | 6H |
| Example 6 | 3-(2-methyl-2-methoxypropionyl)-9-methylcarbazole | 7H |
| Example 7 | 3-(1-hydroxycyclohexanoyl)-9-butylcarbazole | 8H |
| Example 8 | 1,6-bis(9-methyl-3-carbazolyl)-2,5-bis (diethylamino)hexane-1,6-dione | 8H |
| Example 9 | 2,7-bis(1-(9-butyl-3-carbazolyloyl) isopropyl)-2,7-dimethyl-3,6-dioxaoctanol | 7H |

The superior hardness when the photoinitiator of the invention was used is apparent from the results.

EXAMPLES 10 TO 18

A resin mixture composed of 80 parts of NK-ester UVX-2 (epoxy acrylate (m.w.=1500) available from Shinnakamura Kagaku), 20 parts of trimethylolpropane triacrylate, 70 parts of TiO₂, 6 parts of N-methyldiethanolamine and 6 parts of photoinitiator as indicated in Table II was applied to paper using a film-drawing device to a thickness of 10 mµ. These films were irradiated with a mercury high pressure lamp (Toshiba; Model H-400P) for 30 seconds (distance=15 cm). The pencil hardness of the hardened films was then measured, and the results are shown in Table II.

TABLE II

| Example No. | Photoinitiator | Pencil hardness |
| --- | --- | --- |
| Control 1 | Benzophenone | 5B |
| Control 2 | 1-(2-methyl-2-morpholino propionyl)-4-methylthiobenzene | HB |
| Example 10 | 3-(2-methyl-2-morpholino-propionyl)-9-methylcarbazole | 9H |
| Example 11 | 3,6-bis(2-methyl-2-morpholino-propionyl)-9-methylcarbazole | 8H |
| Example 12 | 3-(2-methyl-2-morpholino-propionyl)-9-butylcarbazole | 9H |
| Example 13 | 3-(2-methyl-2-diethanolamino-propionyl)-4-methylcarbazole | 8H |
| Example 14 | 3,6-bis(2-methyl-2-morpholino-propionyl)-9-benzoylcarbazole | 7H |
| Example 15 | 3-(2-methyl-2-allyloxypropionyl)-9-methylcarbazole | 6H |
| Example 16 | 1,4-bis(9-butyl-3-carbazolyl)-2,3-dihydroxybutane-1,4-dione | 7H |
| Example 17 | 1,4-bis(1-(9-methyl-3-carbazolyloyl) isopropyl) piperidine | 8H |
| Example 18 | N,N'-dimethyl-N,N'-bis(1-(9-methyl-3-carbazolyloyl) isoporopyl) ethylenediamine | 7H |

The superior hardness when the photoinitiator of the invention was used is apparent from the results.

EXAMPLES 19 TO 26

A resin mixture composed of 80 parts of NK-ester U-108A (urethane acrylate (m.w.=1500) available from Shinnakamura Kagaku), 20 parts of trimethylolpropane triacrylate, 22 parts of phthalocyanine blue (Dainichiseika; SR-5020), 7 parts of ethyl-4-dimethylaminobenzoate and 7 parts of photoinitiator as indicated in Table III was applied to paper using a film-drawing device to a thickness of 10 mµ. These films were irradiated with a mercury high pressure lamp (Toshiba; Model H-400P) for 30 seconds (distance=15 cm). The pencil hardness of the hardened films was measured, and the results are shown in Table III.

TABLE III

| Example No. | Photoinitiator | Pencil hardness |
| --- | --- | --- |
| Control 1 | Benzophenone | 2B |
| Control 2 | 1-(2-methyl-2-morpholino-propionyl)-4-methylthiobenzene | 2H |
| Example 19 | 3-(2-methyl-2-dimethylamino-propionyl) carbazole | 6H |
| Example 20 | 3-(2-methyl-2-morpholino-propionyl)-9-methylcarbazole | 7H |
| Example 21 | 3-(2-methyl-2-morpholino-propionyl)-9-butylcarbazole | 7H |
| Example 22 | 3-(2-ethyl-2-piperidino-propionyl)-9-butylcarbazole | 6H |
| Example 23 | 3-(2-methyl-2-piperadino-propionyl-6-nitro-9-methylcarbazole | 5H |
| Example 24 | 3-(2-methyl-2-hydroxy-propionyl)-9-methylcarbazole | 6H |
| Example 25 | 1,4-bis(9-butyl-3-carbazolyl)-2,3-dihydroxybutane-1,4-dione | 5H |
| Example 26 | 1,4-bis(1-(9-methyl-3-carbazolyloyl) isopropyl) piperidine | 5H |

The superior hardness when the photoinitiator of the invention was used is apparent from the results.

Having regard to the foregoing disclosure, the following is claimed as inventive and patentable embodiments thereof:

1. A photopolymerizable prepolymer composition comprising a photoinitiator for the photopolymerization of unsaturated compounds having one of the formulae:

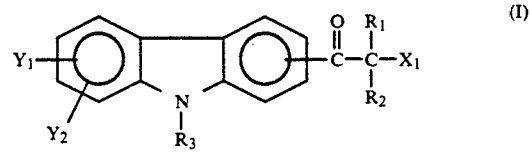

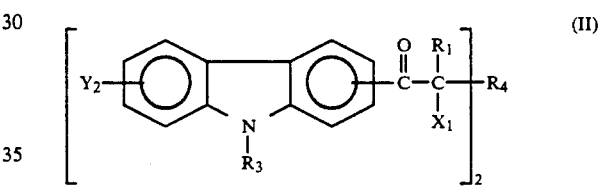

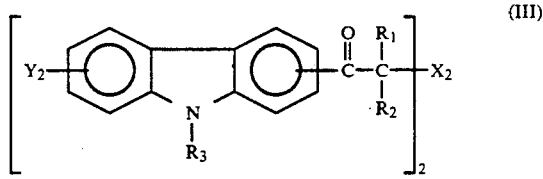

wherein:
R₁ and R₂ are each alkyl having from one to about eighteen carbon atoms; or are taken together to form alkylene having from about two to about twelve carbon atoms;

R₃ is selected from the group consisting of hydrogen; alkyl having from one to about eighteen carbon atoms; and acyl having from about two to about twelve carbon atoms;

X₁ is —OR₅ or

in which R₅ is selected from the group consisting of hydrogen; alkyl and alkenyl having from one to about eighteen carbon atoms; and R₆ and R₇ are selected from the group consisting of alkyl; hydroxyalkyl having from one to about eighteen carbon atoms; and R₆ and R₇ taken together to form alkylene having from about two to about twelve carbon atoms; and oxadialkylene and iminodialkylene having from four to about twenty-four carbon atoms;

$Y_1$ is hydrogen or

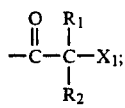

$Y_2$ is selected from the group consisting of hydrogen, halogen, and nitro;

$R_4$ is a direct linkage (—) or alkylene having from about two to about twelve carbon atoms;

$X_2$ is —O—$R_8$—O— or

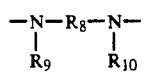

in which:

$R_8$ is alkylene having from about two to about twelve carbon atoms;

$R_9$ and $R_{10}$ are alkyl having from one to about eighteen carbon atoms; or are taken together to form alkylene having from about two to about twelve carbon atoms;

and an unsaturated compound having at least one ethylenic double bond that is photopolymerizable to form a polymer.

2. A photopolymerizable prepolymer composition comprising a photoinitiator according to claim 1 in which the unsaturated compound is a monomer.

3. A photopolymerizable prepolymer composition comprising a photoinitiator according to claim 1 in which the unsaturated compound is a prepolymer.

4. A photopolymerizable prepolymer composition comprising a photoinitiator according to claim 1 in which the unsaturated compound is an unsaturated carboxylic acid ester.

5. A photopolymerizable prepolymer composition comprising a photoinitiator according to claim 4 in which the unsaturated carboxylic acid is acrylic acid ester.

6. A photopolymerizable prepolymer composition comprising a photoinitiator according to claim 4 in which the unsaturated carboxylic acid is methacrylic acid ester.

7. A photopolymerizable prepolymer composition comprising a photoinitiator according to claim 1 also containing a secondary or tertiary alkyl or hydroxyalkyl amine.

8. A process for photopolymerizing an unsaturated compound having at least one photopolymerizable ethylenic double bond, which comprises initiating the unsaturated compound with actinic light in the presence of a photoinitiator for the photopolymerization of unsaturated compounds having one of the formulae:

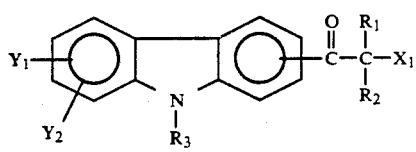
(I)

-continued

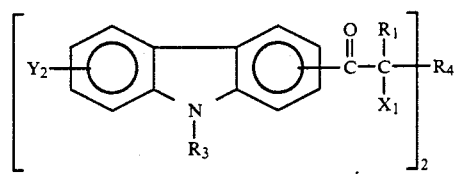
(II)

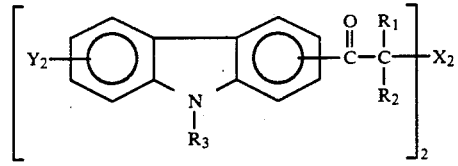
(III)

wherein:

$R_1$ and $R_2$ are each alkyl having from one to about eighteen carbon atoms; or are taken together to form alkylene having from about two to about twelve carbon atoms;

$R_3$ is selected from the group consisting of hydrogen; alkyl having from one to about eighteen carbon atoms; and acyl having from about two to about twelve carbon atoms;

$X_1$ is —OR$_5$ or

in which $R_5$ is selected from the group consisting of hydrogen; alkyl and alkenyl having from one to about eighteen carbon atoms; and $R_6$ and $R_7$ are selected from the group consisting of alkyl; hydroxyalkyl having from one to about eighteen carbon atoms; and $R_6$ and $R_7$ taken together to form alkylene having from about two to about twelve carbon atoms; and oxadialkylene and iminodialkylene having from four to about twenty-four carbon atoms;

$Y_1$ is hydrogen or

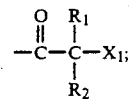

$Y_2$ is selected from the group consisting of hydrogen, halogen, and nitro;

$R_4$ is a direct linkage (—) or alkylene having from about two to about twelve carbon atoms;

$X_2$ is —O—$R_8$—O— or

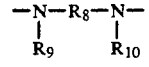

in which:

$R_8$ is alkylene having from about two to about twelve carbon atoms;

$R_9$ and $R_{10}$ are alkyl having from one to about eighteen carbon atoms; or are taken together to form alkylene having from about two to about twelve carbon atoms.

9. A photopolymerizable prepolymer composition according to claim 1, in which the photoinitiator has formula I.

10. A photopolymerizable prepolymer composition according to claim 1, in which the photoinitiator has formula II.

11. A photopolymerizable prepolymer composition according to claim 1, in which the photoinitiator has formula III.

* * * * *